(12) United States Patent
Bogaerts et al.

(10) Patent No.: US 10,123,918 B2
(45) Date of Patent: Nov. 13, 2018

(54) CLOSURE TAPE WITH PATTERNED ADHESIVE

(75) Inventors: Bert Bogaerts, Boechout (BE); Johan Van Steele, Ravels (BE)

(73) Assignee: Avery Dennison Corporation, Glendale, CA (US)

( * ) Notice: Subject to any disclaimer, the term of this patent is extended or adjusted under 35 U.S.C. 154(b) by 381 days.

(21) Appl. No.: 14/005,599

(22) PCT Filed: Mar. 22, 2012

(86) PCT No.: PCT/US2012/030168
§ 371 (c)(1),
(2), (4) Date: Sep. 17, 2013

(87) PCT Pub. No.: WO2012/129428
PCT Pub. Date: Sep. 27, 2012

(65) Prior Publication Data
US 2014/0010984 A1    Jan. 9, 2014

Related U.S. Application Data

(60) Provisional application No. 61/466,042, filed on Mar. 22, 2011.

(51) Int. Cl.
*A61F 13/60* (2006.01)
*A61F 13/56* (2006.01)
*C09J 7/29* (2018.01)
*A61F 13/84* (2006.01)

(52) U.S. Cl.
CPC .......... *A61F 13/60* (2013.01); *A61F 13/5638* (2013.01); *A61F 13/5655* (2013.01); *C09J 7/29* (2018.01); *A61F 2013/8497* (2013.01); *C09J 2201/28* (2013.01); *Y10T 428/1476* (2015.01)

(58) Field of Classification Search
CPC .................. A61F 13/5622; A61F 13/60; A61F 2013/8497; C09J 7/0296; C09J 2201/28; Y10T 428/1476; Y10T 428/14
See application file for complete search history.

(56) References Cited

U.S. PATENT DOCUMENTS

| 4,299,223 A | * | 11/1981 | Cronkrite ...................... 604/390 |
| 5,057,097 A | | 10/1991 | Gesp |
| 5,690,628 A | | 11/1997 | Huskey et al. |
| 5,720,739 A | | 2/1998 | Hilston et al. |
| 5,944,707 A | * | 8/1999 | Ronn ............................. 604/386 |

(Continued)

FOREIGN PATENT DOCUMENTS

| CN | 101242796 A | 8/2008 |
| WO | 2004072346 A2 | 8/2004 |

(Continued)

*Primary Examiner* — Patricia L. Nordmeyer
(74) *Attorney, Agent, or Firm* — Avery Dennison Corporation

(57) ABSTRACT

Various fastening tape closure assemblies are described. The closure tapes are useful in the manufacture of disposable articles, and particularly disposable diapers. The closure tapes generally include a fastening tape and a release tape that at least partially covers the fastening tape during storage and transport of the tape and/or the disposable article. The release tapes include a layer of adhesive for bonding to a region of a diaper. The adhesive layer is in a patterned configuration.

12 Claims, 8 Drawing Sheets

(56) References Cited

U.S. PATENT DOCUMENTS

| | | |
|---|---|---|
| 6,146,369 A | 11/2000 | Hartman et al. |
| 6,221,483 B1 | 4/2001 | Hilston et al. |
| 6,419,667 B1 | 7/2002 | Avalon et al. |
| 6,463,633 B1 | 10/2002 | Sangani et al. |
| 6,524,294 B1 | 2/2003 | Hilston et al. |
| 6,645,338 B1 | 11/2003 | Sangani et al. |
| 2004/0249357 A1 | 12/2004 | Michielsen et al. |

FOREIGN PATENT DOCUMENTS

| | | |
|---|---|---|
| WO | WO 2008156931 A1 * | 12/2008 |
| WO | 2009143325 A1 | 11/2009 |

* cited by examiner

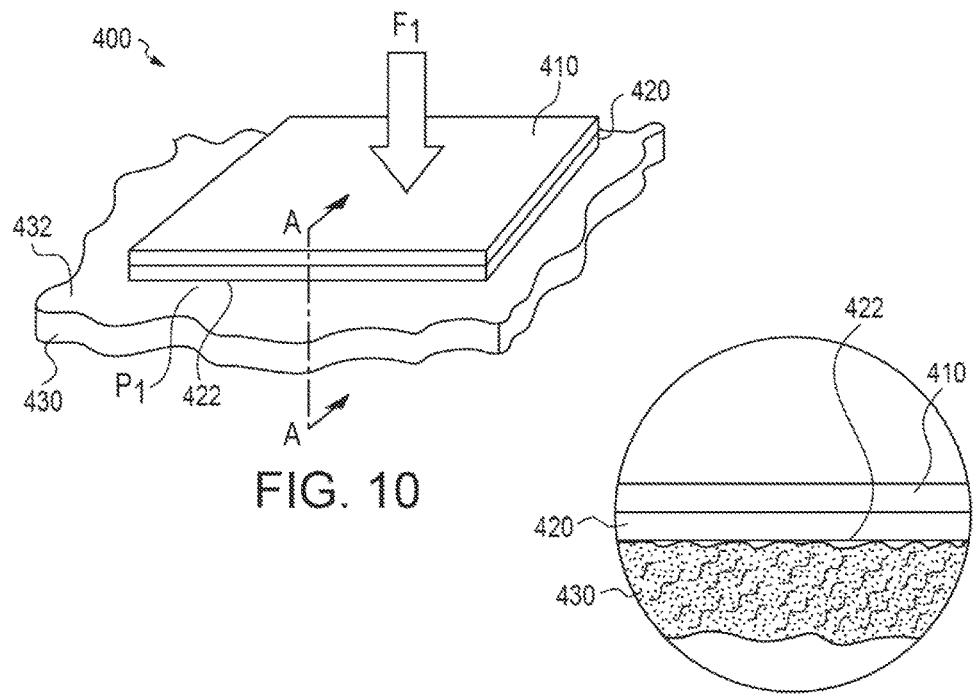
FIG. 10
FIG. 11
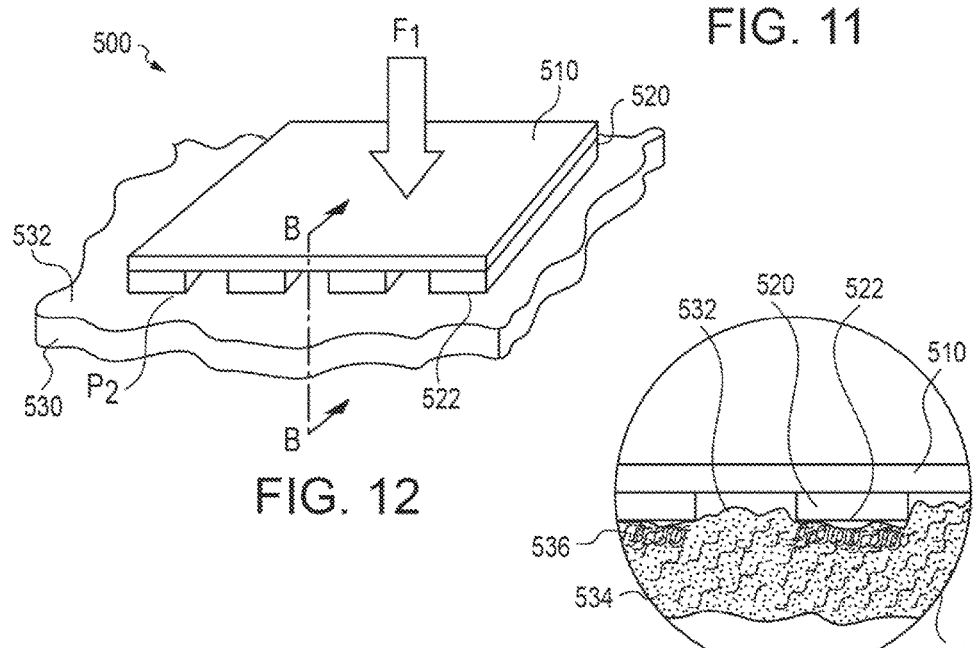
FIG. 12
FIG. 13

CLOSURE TAPE WITH PATTERNED ADHESIVE

CROSS-REFERENCE TO RELATED APPLICATION

The present application is a 371 of International Application No. PCT/US2012/030168, which was published in English on Sep. 27, 2012, which claims priority from U.S. Provisional Application No. 61/466,042 filed Mar. 22, 2011, which is incorporated herein by reference in its entirety.

FIELD

The present subject matter relates to a closure tape assembly having a region of patterned adhesive. The closure tapes are useful in disposable articles, and particularly disposable diapers.

BACKGROUND

A typical diaper construction comprises an absorbent pad or batt or the like enclosed in an outer plastic shell or a non-woven backsheet. The backsheet is typically a non-woven fabric laminated with a water impermeable layer such as a polyethylene film. A water permeable inner shell or liner is also provided to promote separation of fluid from the user.

Typical diapers include a fastener system usually in the form of a tape. The fastener tape system generally includes adhesive tabs fastened to one end of the diaper assembly construction at each lateral side of the diaper in a permanent "factory joint" by the diaper manufacturer using adhesives or other techniques. The tabs typically have a face coated with pressure sensitive adhesive. The tabs are releasably attachable to the other end of the diaper to allow unfastening to inspect the diaper in a nonpermanent "user joint" followed by refastening if indicated.

The user joint may be formed by direct connection of the tab to the diaper outer surface whether the outer surface is formed of a plastic film or a non-woven backsheet. In the case of plastic film shells, it is typical to provide a "landing zone" for the tab to form the user joint. The landing zone may provide a plastic surface of a non-woven surface and may comprise a knit type fabric landing pad.

Securing a fastener to a diaper at the factory joint is typically performed so as to provide a strong and durable affixment. Several techniques have been used including mechanical bonding procedures and the use of high strength adhesives.

A recent trend in diaper construction is the use of increasingly softer materials. This is typically achieved by utilizing nonwoven materials having relatively high degrees of loft. Although no standard definition of loft exists, typically, high loft nonwovens have relatively low densities. The term "high loft" when referring to nonwoven materials typically refers to any fiber structure containing more air than fiber. Regardless of a precise definition, it is difficult to form a factory joint by bonding a fastener such as a tape fastener to a high loft nonwoven material. This is believed to be due to the difficulty in contacting the adhesive face of the fastener with a sufficient number of fibers in the nonwoven material. Due to the high loft of certain nonwoven materials, a significant proportion of the fibers reside relatively far underneath the outer surface of the nonwoven. Thus, in forming a factory joint and in order to reach the fibers residing well under the nonwoven outer surface, relatively high lamination forces must be applied between the adhesive face of the fastener and the nonwoven.

Furthermore, many adhesives that are used to bond fasteners with a nonwoven material to form a factory joint are formulated to have a relatively high internal strength. A consequence of this is that the adhesives are relatively hard and resistant to flow. Accordingly, during formation of a factory joint, very high lamination forces must be used in order for the adhesive to sufficiently flow and thereby bond with the fibers of the nonwoven.

Increasing lamination force typically increases demands on manufacturing equipment and power requirements. Moreover, if the new required lamination forces are sufficiently high, process equipment may need to be modified or entirely replaced with larger equipment. As will be appreciated, modifying or replacing equipment is costly and undesirable. In addition, high lamination forces may also damage the fastener or components of the fastener. For example, if the fastener includes one or more regions of mechanical fasteners such as hook and loop type fasteners, damage to the hook members can occur. Specifically, after the fastener has been attached to a diaper and folded or placed in a stored position, if high lamination forces are applied to the fastener, the hook members and potentially also the loop members can become deformed or distorted. Such damage typically results in nonfunctionality of the mechanical fasteners. Furthermore, high lamination forces may also detrimentally impact conversion speeds. Accordingly, a need exists for a strategy by which fasteners can be securely adhered to high loft nonwoven materials, while avoiding the use of relatively high lamination forces. In addition, a need exists for a technique by which relatively hard adhesives can be securely adhered to nonwovens and particularly, to high loft nonwoven materials, while avoiding the use of relatively high lamination forces.

Reducing costs is a concern in nearly every diaper manufacturing process. Since most processes are high volume, even relatively small reductions in cost per unit can result in significant savings when large numbers of units are produced. Although many cost efficient processes are known for diaper manufacturing, a need remains for further strategies and techniques for reducing costs associated with diapers and related fastening systems.

SUMMARY

The difficulties and drawbacks associated with previous fastener systems and methods of forming factory joints are addressed in the present tape closure assembly.

In one aspect, the present subject matter provides a composite tape from which a closure tab for disposable articles can be cut. The tape comprises a fastening tape defining a distal end and an opposite proximal end. The fastening tape includes a backing film, and an adhesive layer disposed on at least a portion of the backing film. The tape also comprises a release tape defining a distal end and an opposite proximal end. The release tape includes a backing film, an adhesive layer disposed on a first face of the backing film, and a hinge component disposed at the proximal end of the release tape, the release tape also defining a second face that is oppositely directed from the first face. The fastening tape and the release tape are sized and configured for attachment to one another such that the hinge component of the release layer contacts the adhesive layer of the fastening tape and is adhesively attached thereto. The adhesive layer of the release tape is arranged in a pattern configuration.

In another aspect, the present subject matter provides a tape closure assembly from which a closure tab for disposable articles can be cut. The tape assembly comprises a fastening tape component defining a proximal end and a distal end, including at least one backing layer, a continuous adhesive layer disposed along at least a face of the backing layer of the fastening tape, and a finger lift disposed at the distal end and accessible along the adhesive layer. The tape assembly also comprises a release tape component defining a proximal end and a distal end, including at least one backing layer, an adhesive layer disposed along at least a face of the backing layer of the release tape, and a hinge component disposed at a proximal end of the release tape and attaching the release tape. The hinge attaches the release tape to the fastening tape. The adhesive layer of the release tape component is arranged in a pattern configuration.

In still another aspect, the subject matter provides a method of increasing lamination pressure when forming a factory joint in which an adhesive face of a tape assembly is adhered to a receiving surface of a disposable article. The method comprises providing a tape assembly including a fastening tape portion and a release tape portion hingedly attached thereto. The release tape portion has an adhesive layer in a pattern configuration defining at least one region of adhesive and at least one region free of adhesive. The method also comprises providing lamination equipment capable of applying a lamination force to a desired location. The lamination equipment includes a pressing die sized and shaped to correspond to the at least one region of adhesive of the release tape. The method additionally comprises positioning the release tape for contact with the article such that the adhesive layer is directed toward the article. And, the method comprises applying a lamination force to the release tape and the article by use of the lamination equipment whereby contact occurs between the at least one region of adhesive and the article and a relatively high lamination pressure is applied to the at least one region of adhesive.

In another aspect, the subject matter provides a tape assembly from which a closure tab for disposable articles can be cut. The tape comprises a fastening tape defining a distal end and an opposite proximal end. The fastening tape includes a backing layer and an adhesive layer disposed on the backing layer. The tape assembly also comprises a release tape defining a distal end and an opposite proximal end. The release tape includes a backing layer, an adhesive layer disposed on a first face of the backing layer, and a hinge component disposed at the proximal end of the release tape. The release tape also defines a second face oppositely directed from the first face. The tape assembly also comprises at least one region of mechanical fasteners extending from the adhesive layer of the fastening tape. The release tape is adhesively attached to the fastening tape by the hinge component of the release layer, the at least one region of mechanical fasteners is disposed between the fastening tape and the release tape, and the adhesive layer of the release tape is arranged in a pattern configuration.

In yet another aspect, the subject matter provides a tape assembly from which a closure tab for disposable articles can be cut. The tape comprises a fastening tape defining a distal end and an opposite proximal end. The fastening tape includes a backing layer, an adhesive layer disposed on the backing layer, and a first finger lift disposed at the distal end of the fastening tape. The tape assembly also comprises a release tape defining a distal end and an opposite proximal end. The release tape includes a backing layer, an adhesive layer disposed on a first face of the backing layer, and a hinge component disposed at the proximal end of the release tape. The release tape also defines a second face oppositely directed from the first face. The tape assembly further comprises a target tape generally disposed between the fastening tape and the release tape. The target tape defines a distal end and an opposite distal end. The target tape includes a backing layer defining first and second oppositely directed faces, an adhesive layer disposed on the first face of the backing layer and a release layer disposed on the second face of the backing layer. The target tape also includes a second finger lift disposed at the distal end of the target tape. The adhesive layer of the release tape is arranged in a pattern configuration.

In still another aspect, the subject matter provides a tape assembly from which a closure tab for disposable articles can be cut. The tape comprises a fastening tape defining a distal end and an opposite proximal end. The fastening tape includes a backing layer and an adhesive layer disposed on the backing layer. The tape assembly also comprises a release tape defining a distal end and an opposite proximal end. The release tape includes a backing layer, an adhesive layer disposed on a first face of the backing layer, and a release layer disposed on a second face of the backing layer opposite the first face. The fastening tape and the release tape are attached to one another by contact between the adhesive layer of the fastening tape and the release tape. The adhesive layer of the fastening tape contacts at least a portion of the release layer of the release tape and a portion of the second face of the backing layer of the release tape. The adhesive layer of the release tape is arranged in a pattern configuration.

The subject matter additionally provides, in another aspect, a tape assembly from which a closure tab for disposable articles can be cut. The tape comprises a fastening tape defining a distal end and an opposite proximal end. The fastening tape includes a backing layer and an adhesive layer disposed on the backing layer the fastening tape also including a region of mechanical fasteners extending from the adhesive layer. The tape assembly also comprises a release tape defining a distal end and an opposite proximal end. The release tape includes a backing layer, an adhesive layer disposed on a first face of the backing layer, and a hinge component disposed at the proximal end of the release tape. The release tape also defining a second face oppositely directed from the first face. The tape assembly a target tape generally disposed between the fastening tape and the release tape. The target tape defines a distal end and an opposite distal end. The target tape includes a backing layer defining first and second oppositely directed faces, an adhesive layer disposed on the first face of the backing layer and a release layer disposed on the second face of the backing layer. The target tape also includes a finger lift disposed at the distal end of the target tape. The target tape is spaced from the hinge component of the release tape and the mechanical fasteners are disposed between the hinge component and the proximal end of the target tape, and the adhesive layer of the release tape is arranged in a pattern configuration.

As will be realized, the subject matter is capable of other and different embodiments and its several details are capable of modifications in various respects, all without departing from the subject matter. Accordingly, the drawings and description are to be regarded as illustrative and not restrictive.

BRIEF DESCRIPTION OF THE DRAWINGS

FIG. 10 is a schematic illustration of a conventional fastener assembly during an adhesive lamination operation in which a lamination force $F_1$ is applied.

FIG. 11 is a schematic side elevational view of the assembly depicted in FIG. 10 taken across line AA illustrating contact between an adhesive face of the assembly and a nonwoven substrate.

FIG. 12 is a schematic illustration of a preferred embodiment fastener assembly during an adhesive lamination operation in which a lamination force $F_1$ is applied.

FIG. 13 is a schematic side elevational view of the assembly depicted in FIG. 12 taken across line BB illustrating contact between an adhesive face of the assembly and a nonwoven substrate.

DETAILED DESCRIPTION OF THE EMBODIMENTS

Figure 1:
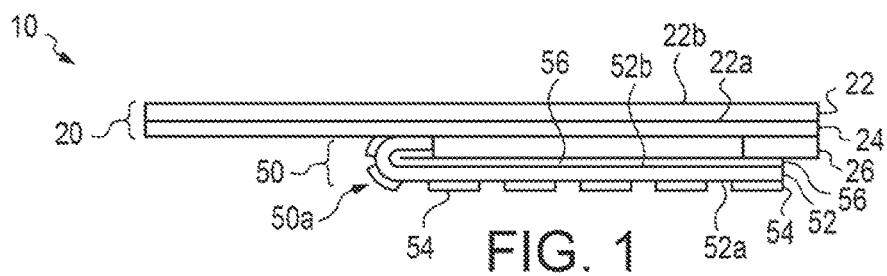
FIG. 1 is a schematic cross sectional view of a preferred embodiment tape closure assembly in accordance with the present subject matter.

The present subject matter generally relates to a tape closure assembly system that is particularly adapted for use with disposable absorbent articles such as diapers. The preferred embodiment tape closure assemblies comprise a fastening tape component and a release tape component that are attached to one another to form the tape closure assembly.

The preferred embodiment tape closure assemblies utilize a particular configuration that provides a cost savings and also facilitates the use of conventional lamination equipment while providing greater lamination pressures to be achieved. As explained in greater detail herein, using greater lamination pressures enables the use of relatively hard adhesives which are resistant to flow, and/or improves contact and bonding between adhesive faces of fasteners and highly lofted nonwoven materials.

The fastening tape component includes one or more backing or support films and an adhesive layer disposed along one of the faces of the backing film(s). The fastening tape component defines a proximal end at which the component is attached to an article such as a diaper in the noted "factory joint," and an opposite distal end. Disposed at this distal end and along the same face at which is disposed the adhesive, a finger lift component is preferably provided.

The release tape component includes one or more backing or support films and an adhesive layer disposed along one of the faces of the backing film(s). The release tape component includes a hinge component at its proximal end and an opposite distal end. The terms proximal and distal correspond to those of the fastening tape component. Thus, the distal end of the release tape component is the end closest to the distal end of the fastening tape component upon attachment of the components to one another. And the proximal end of the release tape component is the end which is closest to the proximal end of the fastening tape component upon attachment of the components to one another. The release tape component is attached to the fastening tape by orienting the release tape component such that its backing film is facing the adhesive layer of the fastening tape. A majority of the adhesive layer of the release tape component is facing away from the fastening tape component. The distal end of the release tape component is preferably located relative to the distal end of the fastening tape component such that the fastening tape distal end extends slightly beyond the release tape distal end. However, the present subject matter includes configurations in which the release tape component is positioned relative to the fastening tape component such that the distal ends of the components are aligned with one another or substantially so. The subject matter also includes configurations in which the distal end of the release tape extends beyond the distal end of the fastening tape. The fastening tape component and the release tape component are then attached to one another by contacting exposed regions of the adhesive layer of the fastening tape component to corresponding regions of the release tape component. The release tape component may also include a mask or cover layer along an exposed face of the adhesive layer of that component.

Preferably, the release tape is attached or otherwise affixed to the fastening tape at a location between the two ends of the fastening tape. In certain versions of the preferred embodiments, the release tape is attached to the fastening tape at a location that is midway between the two ends of the fastening tape. Thus, in this preferred configuration, the release tape has a length that is significantly less than the length of the fastening tape. This reduction in material of the release tape results in costing savings as compared to tape assemblies having release tape portions that have lengths the same as a corresponding fastening tape, or substantially so.

Another feature of the present subject matter is the use of a patterned adhesive on the release tape. The terms "patterned adhesive" or "pattern configuration" refer to a discontinuous adhesive layer or at least region of a discontinuous adhesive layer on the release tape. Since the adhesive layer is not continuous and thus includes one or more regions which are free of adhesive, cost savings can be achieved since reductions in adhesive amounts will thus follow.

Yet another feature of the present subject matter relates to the use of the patterned adhesive on a release tape portion. For certain adhesive patterns such as rows of adhesive extending across the width of a release tape, in which the rows are spaced apart from one another, by applying a lamination force on only the rows of adhesive and not on the regions separating the rows, relatively high lamination pressures can be achieved. This is possible by use of currently existing lamination equipment. Providing higher lamination pressures is possible by applying lamination forces across a reduced surface area constituted by the regions of adhesive in the patterned adhesive layer. Providing higher or increased lamination pressures promotes bonding between an adhesive face of a tape component and the nonwoven material, and enables the use of harder adhesives, i.e. adhesives that exhibit less flowability, in forming factory joints.

Referring to FIG. 1, a preferred embodiment fastening tape closure assembly 10 is illustrated having a composite construction. The fastening assembly 10 comprises a fastening tape portion 20 having particular features and components, and a release tape portion 50 also having particular features and components. Fastening tape 20 includes a substrate or backing film 22, an adhesive layer 24, and a finger lift 26. The adhesive layer 24 is applied to a fastening surface 22a of the backing film 22. The face or surface 22b of the backing film 22 opposite the fastening surface 22a is preferably an exposed outer surface of the fastening tape 20. Adhesive layer 24 may extend continuously along the entire backing layer 22. Alternatively, adhesive layer 24 may extend partially along backing layer 22. When used in conjunction with an absorbent member such as a diaper, the fastening tape portion 20 is permanently bonded to the edge portion of the absorbent member in the manufacturing process, and preferably by adhesive layer 24.

The backing film 22 can be made of cloth, kraft paper, cellophane film, nonwoven webs, polymeric films or other suitable materials or laminates. The term "laminates" as used herein refers to a wide array of materials and combinations of materials. For example, the term laminates includes but is not limited to polymer webs, nonwoven webs, combinations of polymeric webs and nonwoven webs, and various extrusion laminated products. For example, in forming an extrusion laminated product, a nonwoven material is fed to the nip of cooling rolls for a film extrusion product. The extruded product and nonwoven material are intimately bonded together, to thereby form an extrusion laminated product. The backing film may be nonextensible and formed of conventional polymers such as polypropylene, polyvinyl chloride, polyethylene terephthalate, and polyethylene film. In another embodiment, the backing film 22 is extensible. Extensible films include extensible nonwoven and woven fabric and polymeric films, such as those described in U.S. Pat. No. 6,669,887. It will be appreciated that in no way is the subject matter limited to these materials. A release coating is preferably provided on a back side surface, i.e. surface 22b, of the backing film. For example, a silicone or carbamate coating may be applied to the back side surface to promote deployment of the fastening tape.

The adhesive layer 24 preferably comprises an adhesive having a peel strength that is sufficient to permanently attach the backing film to the outer surface of the absorbent article. The adhesive used may be any conventional adhesive, including pressure sensitive adhesives and non-pressure sensitive adhesives. Suitable pressure sensitive adhesives include acrylic resin and natural or synthetic based rubber adhesives. In one embodiment, the adhesive is a hot melt pressure sensitive adhesive of the A-B-A block copolymer type comprising an elastomeric B-block derived from isoprene and thermoplastic A-blocks derived from styrene as disclosed in U.S. Pat. No. 3,932,328. Illustrative rubber based adhesives include styrene-isoprene-styrene, styrene-butadiene-styrene, styrene-ethylene/butylenes-styrene and styrene-ethylene/propylene-styrene that may optionally contain diblock components such as styrene isoprene and styrene butadiene. The adhesive layer may be applied using hot-melt, solvent or emulsion techniques. It will be appreciated that in no way is the subject matter limited to these materials.

The fastening tape 20 at its free or distal end may include a finger lift 26. The finger lift 26 is provided to allow easy removal of the adjacent portion of the fastener tape from a surface from which the tape section is attached in the storage position or to facilitate reopening. In one embodiment, the finger lift comprises a thin film, for example a polypropylene film, non-woven, or paper. The thin film is attached to the fastening tape at the free end of the backing film. In another embodiment, the finger lift comprises an adhesive-free section of the backing film. In yet another embodiment, the finger lift comprises a folded over section of the backing film to which the adhesive layer is applied.

In one embodiment of the subject matter, fastening tape 20 is a stretchable tape that includes an extensible layer. Stretchable tapes are described in U.S. Pat. Nos. 6,463,633, 6,419,667 and 6,146,369. The stretchable tape allows greater size adjustments for a disposable diaper or garment.

Referring further to FIG. 1, the preferred fastening tape closure assembly 10 further includes a release tape portion 50 for selective engagement with the fastening tape 20. Release tape 50 includes a backing film 52 to which an adhesive layer 54 is applied. The adhesive layer 54 is preferably a patterned adhesive or in a pattern configuration as described in greater detail herein. Backing film 52 may comprise any of the materials described above with reference to backing film 22. Adhesive layer 54 may comprise any of the adhesives described above with reference to adhesive layer 24. Further, a release coating 56 may be applied to a contacting surface 52b of the backing film 52. The face or surface 52a opposite the contacting surface 52b is the face of the backing film 52 on which is disposed the adhesive layer 54.

The release tape 50 also includes a hinge region 50a generally in the form of a raised region of material extending from the contacting surface 52b of the backing film 52. Preferably, the hinge region 50a is provided by a proximal end or edge region of the backing film 52 and the adhesive layer 54 that is folded onto itself as shown in FIG. 1. The outwardly directed region of the adhesive layer 54 along the proximal end or hinge region 50a of the release tape 50 is illustrated. It will be appreciated that in no way is the subject matter limited to the particular hinge construction shown in the accompanying figures. For example, instead of forming a hinge by folding over an edge of the release tape, one or more layers of a backing film or other material(s) could be positioned on the backing film 52 of the release tape 50 at the appropriate location.

As previously explained, the preferred embodiment fastening tape closure assembly 10 utilizes a configuration in which the length of the release tape 50 is significantly less than the length of the fastening tape 20. Accordingly, the release tape 50 is preferably attached at the hinge location

50a which is located approximately at or near the midpoint of the length of the fastening tape 20. Furthermore, as depicted in the referenced figures, the adhesive layer 54 associated with the release tape is in the form of a patterned adhesive layer.

Figure 2:
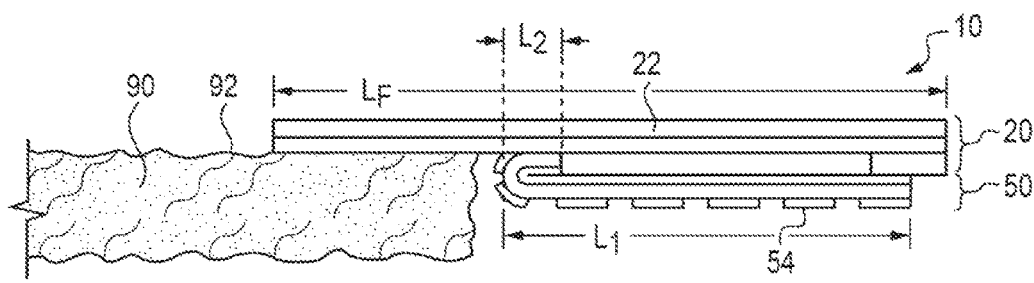
FIG. 2 is a schematic cross sectional view of the preferred tape assembly depicted in FIG. 1, partially attached to an edge region of an absorbent member.

FIG. 2 illustrates the fastening tape 20 attached to an absorbent member 90, and preferably to an outer surface 92 of a diaper. This attachment as noted, is preferably a permanent attachment and partially constitutes the previously mentioned "factory joint." FIG. 2 also depicts engagement of the release tape 50 to the fastening tape 20. FIG. 2 also illustrates in greater detail the relative lengths of the fastening tape 20 and the release tape 50 of the preferred embodiment closure assembly 10. The length of the fastening tape is designated as $L_F$. The length of the release tape is generally the sum of the length of the release tape from the distal end to the hinge 50a, denoted as $L_1$ and the length of the remaining portion of the release tape shown as $L_2$. Thus, the length of the release tape $L_R$ is generally $L_1+L_2$. Preferably, $L_R<L_F$. More preferably $L_R \leq 90\%\ L_F$, more preferably $L_R \leq 80\%\ L_F$, more preferably $L_R \leq 70\%\ L_F$, and most preferably $L_R \leq 60\%\ L_F$.

Figure 3:
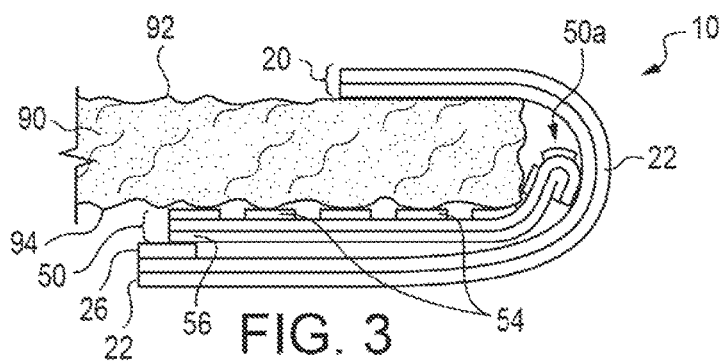
FIG. 3 is a schematic cross sectional view of the preferred tape assembly of FIGS. 1 and 2 fully attached to the absorbent member and in a storage position, and prior to use by a consumer.

The completed attachment of the fastening tape closure assembly 10 to the absorbent member 90 is shown in FIG. 3 in which the fastening tape 20 is folded over and the release tape 50 is secured to the absorbent member 90 in a stored position by the adhesive layer 54 contacting an inner surface 94 of the absorbent member 90. The fastening tape 10 remains in this folded condition up to the point in time that the diaper is used. Upon deployment, the distal end section of the fastening tape 20 is extended from its folded condition. Finger lift 26 is used to initiate pulling the end section from its folded position. Specifically, referring to FIG. 3, upon wishing to deploy the tape from its stored position, a user grasps the distal end of the fastening tape 20 generally at the finger lift 26 and pulls the corresponding portion of the fastening tape 20 away from the absorbent member 90. Separation of the tape portions 20 and 50 continues until the point of separation is at the location of the hinge region 50a.

Figure 4:
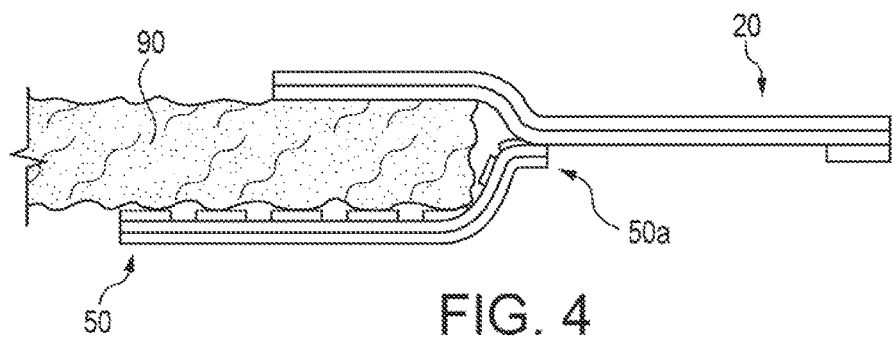
FIG. 4 is a schematic cross sectional view of the preferred tape assembly and absorbent member of FIG. 3, in a use or deployed position.

FIG. 4 illustrates the preferred tape closure assembly 10 in its deployed position and ready for releasably securing a region of the absorbent member 90 to another region of the member such as at landing zone (not shown).

The distal end portion or finger lift 26 of the fastening tape 20 may be in the form of a serrated or wavy edge for example. This configuration promotes separation from adjacent regions of the backing film 56 of the release tape 50 when the fastening tape 10 is in its stored position as depicted in FIG. 3. In addition, a serrated or wavy configuration may provide an aesthetically pleasing appearance to the distal end of the fastening tape 20, particularly when the fastening tape 20 is secured to another region of the absorbent member or diaper such as the landing zone. The appearance of the distal end of the fastening tape 20 can be further altered and/or improved by utilizing a finger lift 26 that is colored, for example blue or pink. Providing a colored or visually accentuated finger lift 26 also serves to aid in identifying the location of the distal end of the fastening tape 20 upon attachment to the landing zone or other diaper area. The finger lift 26 can be provided in a wide array of shapes, sizes, and configurations. In one version of the tape closure assembly, the finger lift is provided such that the thickness of the finger lift is equal or approximately so, to the thickness of the release tape. Referring to FIG. 1 in this regard, the finger lift 26 is selected or otherwise formed such that the thickness of the finger lift 26 is equal or approximately equal to the thickness of the release tape as measured at a distal end of the release tape, i.e., at an end opposite the hinge region. It will be understood that the various tape closure assemblies can be free of finger lift(s). For example, the present subject matter includes a tape closure assembly such as assembly 10 depicted in FIG. 1, which is devoid of a finger lift 26. It is also contemplated that a region of adhesive or an adhesive pattern can be utilized in place of the finger lift 26, on the fastening tape 20.

Figure 5:
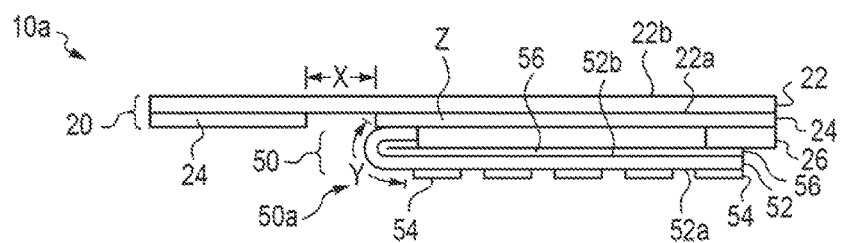
FIG. 5 is a schematic cross sectional view of a variation of the preferred embodiment tape closure assembly depicted in FIG. 1.

FIG. 5 illustrates a variation of the tape closure assembly illustrated in FIG. 1. In this variant assembly, designated as 10a, one or more adhesive-free regions are provided along the backing film 22 of the fastening tape portion 20, and/or along the backing film 52 of the release tape portion 50. The adhesive-free region along the backing film 22 is illustrated in FIG. 5 as region X. The adhesive-free region along the backing film 52 is illustrated in FIG. 5 as region Y. Both of the adhesive-free regions X and Y extend along their respective backing films, from the hinge region 50a toward the proximal end of the assembly. Region X is defined on a face of the backing film 22 directed toward the release tape portion 50. Region Y is defined on a face of the backing film 52 directed toward the fastening tape portion 20. The reference to "directed toward" refers to the tape closure assembly when in its attachment position as depicted in FIG. 3. The linear distance of the adhesive-free regions X and Y as measured along their respective backing films, can be equal to one another or different than one another. Although not wishing to be bound to any particular length or distance, typically, the linear distance of the adhesive-free regions X and Y is at least about 1 mm, and generally at least about 5 mm. The adhesive-free regions X and/or Y may extend along their respective backing films toward the proximal end of the tape closure assembly for a distance of up to about 10 mm, and in certain applications up to about 20 mm. Region Z in FIG. 5 represents a region of adhesive. The region Z of adhesive is utilized to achieve adhesive attachment at the hinge region between the fastening tape and the release tape. It will be understood that the region Z of adhesive may be initially applied to either of those components during production of the tape closure. The use of adhesive-free regions X and/or Y in the tape closure assembly 10a has been found to promote stability of the closure assembly during and after storage, and particularly in wound storage configurations such as on spools. The adhesive-free regions X and/or Y can be formed by adhesive patterning methods. It is also contemplated to provide adhesive-free regions X and/or Y by applying adhesive deactivating agents or components on the adhesive layers 24 and/or 54 in one or both of regions X and Y.

In certain versions of the tape closure assembly, if X=0, such that the fastening tape 20 is fully coated with adhesive, then Y>0, such that an adhesive-free region is defined on the release tape 50. Alternatively, if X>0, such that an adhesive-free region is defined on the fastening tape 20, then the area on the release tape 50 corresponding to region Y (and including the Y-bond) should contain adhesive to bond the release tape 50 to the fastening tape 20 in the region X of the fastening tape 20. A reason for this particular configuration is roll stability and avoiding having fastening tape adhesive and release tape adhesive superimposed onto one another. Superimposing regions of fastening tape adhesive and release tape adhesive would create a thick spot or region in the tape resulting in instability of the roll as in telescoping. This same alignment strategy of adhesive and adhesive-free regions can be applied to mechanical closure systems such as those depicted in FIGS. 15 and 18, herein. For example, mechanical closures can be aligned as in FIG. 15 in different lanes, or as in FIG. 18 in one hook zone. Such hook zone can be aligned as in FIG. 18 adjacent to the Y-bond, or adjacent to the finger lift in an alternative version.

The fastening tape 20 and the release tape 50 can be provided in separate rolled configurations, or preferably, engaged to one another as shown in FIG. 1 and then provided in a roll form. The width of the roll of closure tape of the present subject matter depends on the intended application. Typically, the rolls that are used for closure tabs for disposable articles have a width in the range of about 30 to about 100 mm. In one embodiment, the width of the rolls is in the range of about 45 to about 75 mm. The closure tape can be provided in a roll, for example, as a disc wound roll or a spool wound roll. The closure tabs of the subject matter can be cut from a stock roll. In use, a segment of the roll of composite closure tape is cut from the roll in a desired length.

Figure 6:
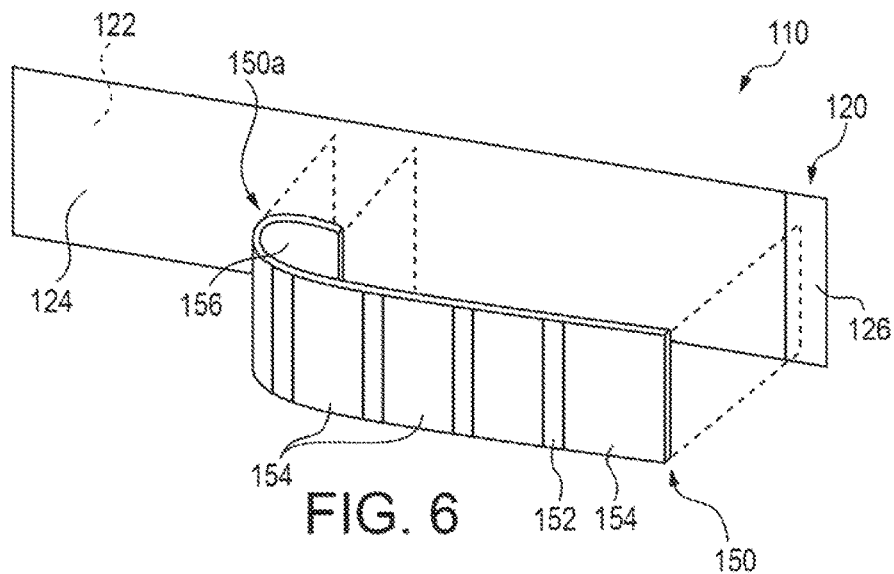
FIG. 6 is an exploded perspective schematic view of another preferred embodiment tape assembly.
Figure 7:
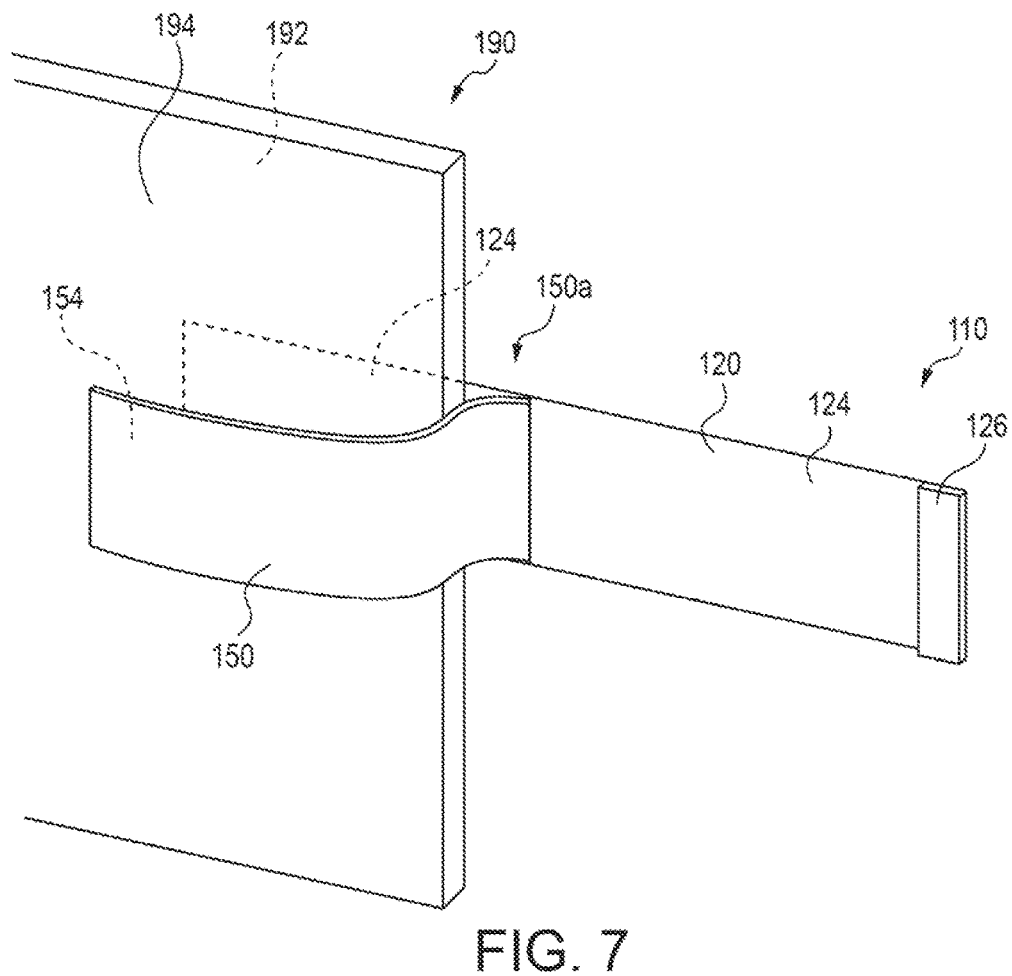
FIG. 7 is a perspective schematic view of the preferred embodiment tape assembly shown in FIG. 6, attached to an edge region of an absorbent member.

FIGS. 6 and 7 schematically illustrate another preferred embodiment fastening assembly 110 in accordance with the subject matter. The fastening assembly 110 includes a fastening tape portion 120 and a release tape portion 150, generally as previously described in conjunction with the assembly 10 depicted in FIGS. 1-4. The fastening tape 120 includes a backing film 122 and an adhesive layer 124 disposed therein. A finger lift 126 is preferably provided along a distal end of the fastening tape 120. The fastening assembly 110 also includes a release tape portion 150 including a backing film 152 and an adhesive layer 154 disposed thereon. The adhesive layer 154 is preferably a patterned adhesive or in a pattern configuration as described in greater detail herein. A release layer 156 is preferably provided along a face of the backing film 152 opposite the adhesive layer 154. The release tape 150 preferably defines a hinge region 150a at which the release tape 150 is adhesively attached to the fastening tape 120. The fastening assembly 110 is preferably attached to an absorbent member 190 as shown in FIG. 7. In this affixment configuration, the adhesive layer 154 of the release tape 150 contacts a face 194 of the absorbent member 190, and the adhesive layer 124 of the fastening tape 120 contacts an oppositely directed face 192 of the absorbent member 190. As illustrated in FIG. 7, upon deploying the distal end of the fastening tape 120 carrying the finger lift 126, the fastening tape 120 and specifically, the adhesive layer 124, is exposed and ready for attachment to another region (not shown) of the absorbent member 190.

Figure 8:
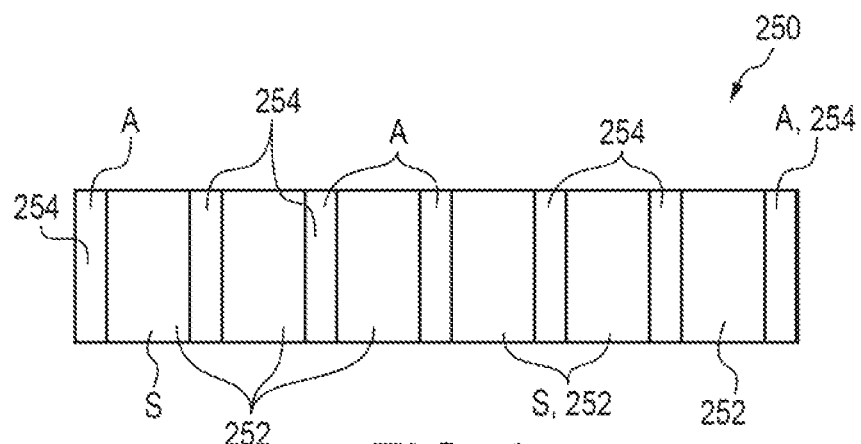
FIG. 8 is a schematic planar view of a release tape portion of a preferred embodiment tape assembly illustrating a preferred adhesive pattern.

In all of the preferred embodiments described herein, the adhesive layer of the release tape, e.g. the adhesive layer 54 of the release tape 50 of the fastener 10 and the adhesive layer 154 of the release tape 150 of the fastener 110, is discontinuous. Preferably, the discontinuous adhesive layer of the release tape portion is in a pattern configuration as follows. FIG. 8 is a schematic planar view of a preferred pattern for the adhesive layer of a release tape portion 250. In this configuration, an adhesive layer 254 is in the form of a plurality of rows or regions, each designated as "A" in FIG. 8. The rows or regions A of the adhesive 254 are disposed on a backing layer 252. The rows A of adhesive 254 are spaced apart from one another by corresponding spaced rows or regions "S". The underlying backing layer 252 is thus visible in rows S. In the adhesive pattern configuration depicted in FIG. 8, the width of the adhesive regions A is less than the width of the spaced regions S. Thus, in this pattern configuration, S>A.

Figure 9:
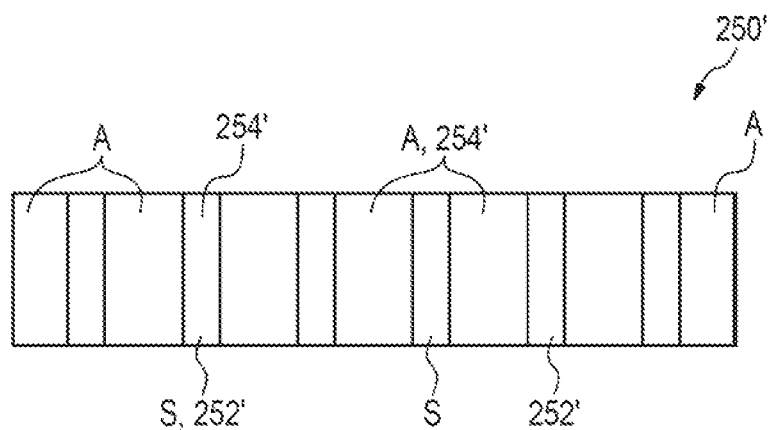
FIG. 9 is a schematic planar view of a release tape portion of another preferred embodiment tape assembly illustrating another preferred adhesive pattern.

FIG. 9 depicts another preferred pattern configuration for the adhesive layer of a release tape 250'. In this version, rows A of adhesive 254' are separated by spaced rows S. An underlying backing layer 252' is visible in the spaced rows S. In this configuration, the width of the adhesive regions A is greater than the width of the spaced regions S and so S<A.

It is also contemplated that the width of the rows of adhesive could be equal to the width of spacing, i.e. S=A.

Although in the adhesive patterns illustrated in FIGS. 8 and 9, the width of each row of adhesive, i.e. row A, is depicted as constant or the same, the subject matter includes patterns in which rows of adhesive are provided in which the width of one or more rows is different. Similarly, the subject matter also includes patterns in which spacing rows, i.e. row S have widths different from one another.

The particular dimensions or proportions for the adhesive rows or regions and for the spacing rows or regions can vary depending upon the end use requirements. However, a preferred ratio of widths for the adhesive rows to the spacing rows is from about 0.5 to about 2.5:1, and more preferably about 1.5:1, respectively.

Although not wishing to be bound to any particular dimensions, in certain preferred versions of a patterned adhesive layer, alternating rows of adhesive and adhesive-free regions are provided. The widths of the adhesive regions are preferably the same for all such regions and range from about 1 mm to about 5 mm, and most preferably about 3 mm. Similarly, the widths of the adhesive-free regions are preferably the same for all such regions and range from about 0.5 mm to about 4 mm, and most preferably about 2 mm. However, it will be appreciated that in no way is the subject matter limited to any particular dimensions for the regions of adhesive and adhesive-free regions.

Furthermore, the present subject matter includes a wide array of adhesive patterns and/or configurations. That is, the subject matter is not limited to the particular patterns depicted in FIGS. 1-9. The pattern configuration of the adhesive layer may take a variety of different forms. For example, in one aspect the pattern configuration may include at least one region of adhesive and at least one region free of adhesive. More specifically, the pattern configuration may include a plurality of adhesive regions and a plurality of adhesive-free regions. The adhesive regions and the adhesive-free regions can be randomly arranged on a face or layer of an underlying substrate, or be arranged in an orderly fashion in which the regions of adhesive are spaced apart from one another by one or more adhesive-free regions.

As previously noted, when adhering an adhesive face of a release tape to a face of a high loft nonwoven material, relatively high lamination pressures must be used to effectively bond adhesive to underlying fibrous regions of the nonwoven. In addition, high lamination pressures may be necessary in order to adhere to certain relatively hard adhesives. Use of the patterned adhesive layers as described herein, and particularly the alternating spaced rows depicted in FIGS. 8 and 9, enable high lamination pressures to be achieved. As will be understood, pressure results from application of a force over a given area. By reducing the area and maintaining a lamination force as previously used, the resulting lamination pressure can be significantly increased. Thus, by using the preferred embodiment tape closure assemblies having discontinuous patterned adhesive layers and corresponding lamination dies, press tools, or pressing dies having faces that contact only the regions of adhesives, currently existing or conventional lamination equipment can be used to provide and apply relatively high lamination pressures.

These features are better understood by reference to FIGS. 10-13 as follows. FIG. 10 is a schematic illustration of a conventional fastener system 400 being laminated to a nonwoven 430. The fastener system 400 includes an outer support layer 410 and an adhesive layer 420 defining an adhesive face 422. During lamination and attachment of the fastening system 400 to the nonwoven 430, the adhesive face 422 of the fastener system 400 is contacted with an outer face 432 of the nonwoven 430. A lamination force $F_1$ is then applied which generally results in a pressure $P_1$ along the interface of the adhesive face and the nonwoven. FIG. 11 is a side elevational view of the fastener system 400 and the nonwoven 430 during lamination. It is evident that typically, contact between the nonwoven 430 and the adhesive face 422 is discontinuous, and generally only fibers along the outer face 432 of the nonwoven are contacted with the adhesive face 422.

FIGS. 12 and 13 illustrate lamination between a preferred embodiment fastener system 500 and a nonwoven 530. Generally, the fastener system 500 comprises an outer support layer 510 and a patterned adhesive layer 520 to defining an adhesive face 522. During lamination and attachment of the fastening system 500 the nonwoven 530, the adhesive face 522 is contacted with an outer face 532 of the nonwoven 530. In this configuration, if the same lamination force $F_1$ is used, a different lamination pressure $P_2$ will result along the interface of the adhesive face 522 and the nonwoven face 532. Specifically, due to the provision of the patterned adhesive layer 520, the lamination pressure $P_2$ associated with the configuration of FIGS. 12 and 13 will be greater than the lamination pressure $P_1$ associated with the configuration of FIGS. 10 and 11. Referring to FIG. 13, a schematic depiction is provided of the effect of a greater lamination pressure $P_2$. In the nonwoven 530, regions of compressed fibers 536 are formed generally corresponding to the location and extent of the adhesive face 522. These regions 536, are compressed relative to other regions such as inner region 534, and are characterized by containing a higher number of fibers per unit volume, i.e. a higher fiber density, than other regions in the nonwoven. Thus, a greater number and greater extent of fibers are bonded to the adhesive face 522. Thus, the use of a patterned adhesive layer as described herein results in greater bonding strength between a fastener and a nonwoven.

Figure 14:
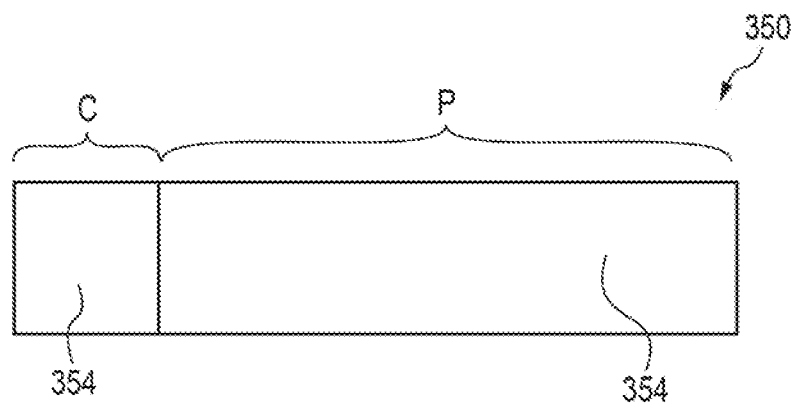
FIG. 14 is a schematic planar view of a release tape portion of another preferred embodiment tape assembly illustrating yet another preferred adhesive pattern.

FIG. 14 is a schematic planar view of a release tape portion 350 of a preferred tape assembly illustrating yet another preferred adhesive pattern. This embodiment includes a region P of the release tape 350 which includes an adhesive layer 354 in a pattern configuration, and one or more region(s) of the release tape 350 in which the adhesive layer 354 is in a continuous layer. These region(s) are denoted as region(s) C in FIG. 14. It will be understood that the release tape 350 can utilize a wide assortment of arrangements and locations for region(s) P and C. Thus, the release tape 350 can include an arrangement in which the area of region C is equal to or greater than that of region P. In addition, each or both of the regions P and C can be in other shapes rather than the square and rectangular shapes as depicted in FIG. 14.

The subject matter also provides methods for conveniently increasing lamination pressures from existing equipment. When laminating adhesive faces having pattern configurations as described herein, a pressing die is used which corresponds to the shape and size of the adhesive regions. Thus, preferably, the pressing die does not extend to or contact regions of the patterned adhesive which are free of adhesive. Specifically, a representative preferred method comprises providing a tape assembly including a fastening tape portion and a release tape portion hingedly attached thereto. The release tape portion has an adhesive layer in a pattern configuration defining at least one region of adhesive and at least one region free of adhesive. The method also comprises providing lamination equipment capable of applying a lamination force to a desired location. The lamination equipment includes a pressing die sized and shaped to correspond to the at least one region of adhesive of the release tape. The method additionally comprises positioning the release tape for contact with the article such that the adhesive layer is directed toward the article. And, the method comprises applying a lamination force to the release tape and the article by use of the lamination equipment whereby contact occurs between the at least one region of adhesive and the article and a relatively high lamination pressure is applied to the at least one region of adhesive.

Yet another advantage associated with the preferred embodiments and particularly the use of patterned adhesive layers is that the adhesive coatweight used in forming such patterns could be increased and the resulting patterned adhesive layer could still provide material and/or cost savings as compared to a corresponding nonpatterned adhesive layer.

In all of the configurations and assemblies described herein, it will be appreciated that one or more layers or regions of a release layer can be incorporated into the various fastening tape closure assemblies. For example, it may be desired to apply a release layer over one, all, or a portion of surfaces that contact an adhesive layer. Alternatively, release materials may be selectively applied upon portions of certain adhesive layers to achieve various effects.

Aspects and features of the preferred embodiments can be utilized in a wide range of fastening and/or tape systems. For example, the use of patterned adhesive layers can be utilized in triple tapes, European duo tape, mechanical tapes, and triple mechanical tapes.

Figure 15:
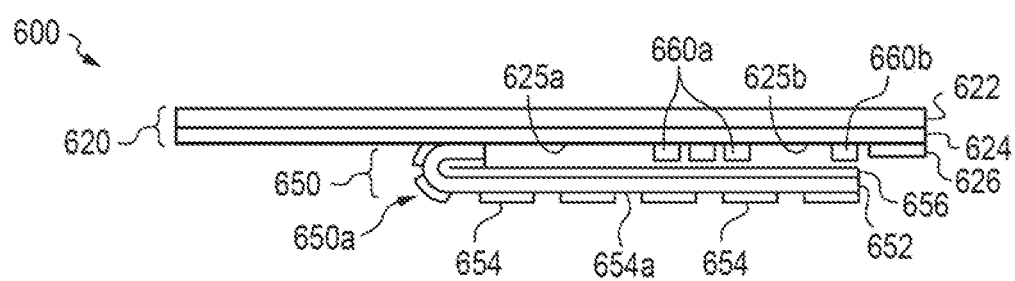
FIG. 15 is a schematic illustration of another preferred embodiment tape assembly in accordance with the present subject matter.

FIG. 15 illustrates another tape configuration using various aspects of the subject matter. Specifically, a preferred embodiment mechanical closure fastening tape 600 is illustrated in FIG. 15. The tape system 600 comprises a fastening tape 620 and a corresponding release tape 650 attached to the fastening tape 620 via a hinge 650*a*. The release tape 650 includes a patterned adhesive that generally includes one or more regions of adhesive 654 and one or more adhesive-free regions 654*a*. The fastening tape 620 includes a backing or substrate 622 and an adhesive layer 624. A finger lift 626 is preferably provided at a distal end of the fastening tape 620 as shown in FIG. 15. The release tape 650 includes a backing film 652. A release layer 656 is provided along a face that is opposite from the patterned adhesive regions 654. The tape system 600 also comprises mechanical fasteners depicted as 660*a* and 660*b*. Preferably, the mechanical fasteners are hook or loop type fasteners as known in the art, and most preferably hook type fasteners. The hook fasteners are preferably arranged in rows such as schematically depicted in FIG. 15 and preferably arranged in at least two regions 660*a* and 660*b* separated by a fastener-free region 625*b*. A portion of the adhesive layer 624 is exposed in the fastener-free region 625*b*. Upon assembly of the tape 600 and attachment of the release tape 650 to the fastening tape 620, the release layer 656 of the release tape 650 contacts the adhesive layer 624 of the fastening tape 620 and promotes retention of the distal end of the release tape 650 to the underside of the fastening tape 620. This is desirable to prevent or significantly reduce the potential for "flagging" of the release layer 650. The term "flagging" refers to unintended separation of the distal end of the release layer 650 from the fastening tape 620. Thus, the region 625*b* of exposed adhesive 624 serves as a bonding area. The preferred tape system 600 also preferably includes an additional fastener-free region 625a such as between the fasteners 660a and the hinge 650a. The region 625a provides additional exposed regions of the adhesive 624 for bonding with the release layer 656 of the release tape 650.

Figure 16:
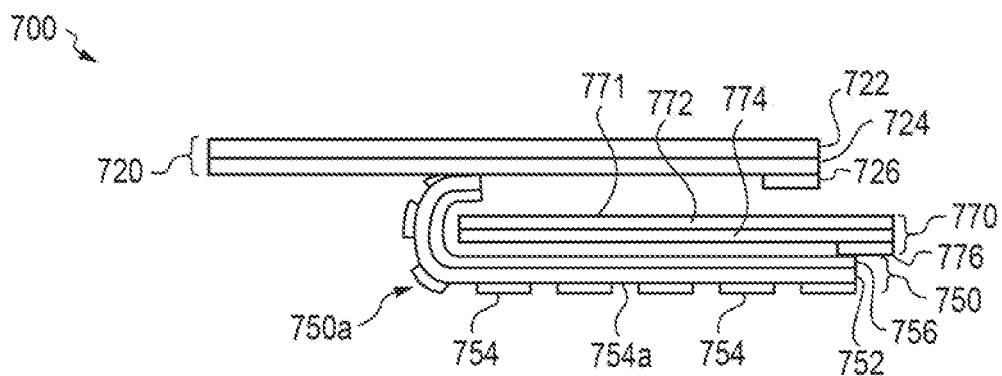
FIG. 16 is a schematic illustration of another preferred embodiment tape assembly in accordance with the present subject matter.

FIG. 16 illustrates a triple tape configuration utilizing various aspects of the subject matter. Specifically, FIG. 16 schematically illustrates a preferred embodiment tape system 700 comprising a fastening tape 720, a release tape 750, and a target tape 770 generally disposed between the fastening tape 720 and the release tape 750. The release tape 750 is attached to the fastening tape 720 via a hinge 750a. The fastening tape 720 includes a backing layer or substrate 722, an adhesive layer 724 and a finger lift 726 disposed at a distal end of the fastening tape 720. The release tape 750 includes a backing film 752 having a release layer 756 and on another face, a patterned adhesive 754. The patterned adhesive 754 includes one or more adhesive regions 754 separated by one or more adhesive-free regions 754a. The patterned adhesive is as described herein. The target tape 770 includes a backing layer 772, an adhesive layer 774, a finger lift 776 disposed at a distal end of the target tape 770, and a release layer 771 disposed on a face of the backing layer 772 that is directed toward the fastening tape 720.

Figure 17:
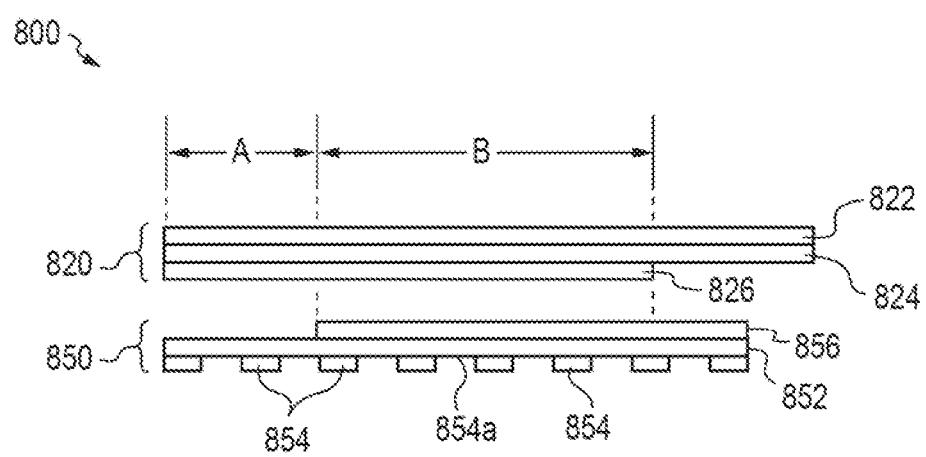
FIG. 17 is a schematic illustration of another preferred embodiment tape assembly in accordance with the present subject matter.

FIG. 17 illustrates yet another tape configuration using various aspects of the subject matter. Specifically a preferred embodiment European duo tape system 800 is illustrated in FIG. 17. The preferred duo tape 800 comprises a fastening tape 820 and a release tape 850. The fastening tape 820 includes a backing 824, a release layer 822 disposed on the backing 824, and an adhesive layer 826 disposed on an opposite face of the backing 824. The adhesive layer 826 extends in regions A and B of the fastening tape 820. The release tape 850 includes a backing layer 852 and a release layer 856 disposed on the backing 852. The release tape 850 also includes a patterned adhesive layer 854 as described herein. The patterned adhesive layer preferably includes one or more regions of adhesive 854 separated by one or more adhesive-free regions 854a. The release layer 856 of the release tape 850 extends within region B and may extend in additional regions such as shown in FIG. 17 in which the release layer 856 extends to the distal end of the release tape 850. However, it is preferred that the release layer 856 does not extend into region A. Upon assembly of the duo tape 800, the fastening tape 820 and the release tape 850 are contacted with one another and adhesively adhered thereto. Due to the presence and location of the release tape 856, during initial use of the tape 800, a user can readily separate the fastener tape 820 and the release tape 850 from one another along region B. However, the two tapes 820 and 850 remain adhesively adhered to one another in the region A.

Figure 18:
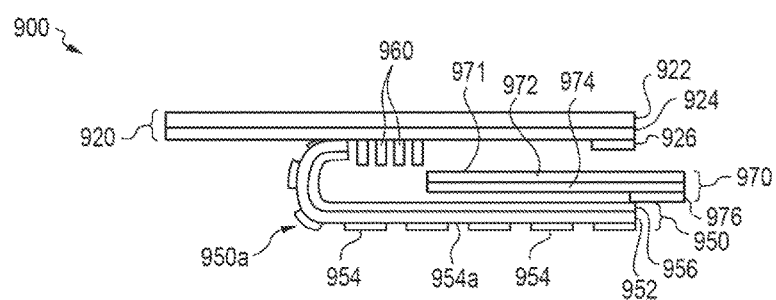
FIG. 18 is a schematic illustration of another preferred embodiment tape assembly in accordance with the present subject matter.

FIG. 18 illustrates another tape configuration using various aspects of the subject matter. Specifically, a preferred embodiment triple mechanical closure fastening tape 900 is depicted in FIG. 18. The tape system 900 comprises a fastening tape 920, a release tape 950, and a target tape 970. The fastening tape 920 includes a backing layer 922 and an adhesive layer 924. The fastening tape 920 also includes an optional finger lift 926 disposed at a distal end of the fastening tape 920. The fastening tape 920 also includes a region of mechanical fasteners 960, which are preferably hook fasteners. The release tape 950 includes a backing layer 952 having a release layer 956 disposed on one face and an adhesive layer 954 disposed on an opposite face of the backing layer 952. The adhesive layer is a patterned adhesive layer as described herein and preferably includes one or more adhesive regions 954 and one or more adhesive-free regions 954a. The release tape 950 also includes a hinge component 950a as previously described, disposed at a proximal end of the release tape 950. The target tape 970 includes a backing layer 972, a release layer 971 disposed on a face of the backing layer 972 directed toward the fastening tape 920, and an adhesive layer 974 disposed on a face of the backing layer 972 directed toward the release tape 950. The target tape 970 also includes a finger lift 976. As shown in FIG. 18, it is preferred that the proximal end of the target tape 970 is spaced from the hinge component 950a a sufficient distance so that the mechanical fasteners 960 do not contact the target tape 970.

It is also contemplated that one or more elastic regions can be provided in the fastening tape portion. The elastic regions can be provided by incorporation of materials exhibiting elastic properties. The elastic regions can also be provided by forming or providing certain structural features into the fastening tape. The elastic regions can also be provided by performing one or more processing operations upon desired regions of the fastening tape. Details as to forming and/or providing elastic regions in fastening tape closure assemblies are provided in U.S. Pat. Nos. 5,057,097; 6,645,338; 6,221,483; 5,690,628; 6,524,294; and 5,720,739 all assigned to Avery Dennison Corporation.

Many other benefits will no doubt become apparent from future application and development of this technology.

All patents, published applications, and articles noted herein are hereby incorporated by reference in their entirety.

It will be understood that any one or more feature or component of one embodiment described herein can be combined with one or more other features or components of another embodiment. Thus, the present subject matter includes any and all combinations of components or features of the embodiments described herein.

As described hereinabove, the present subject matter solves many problems associated with previous type devices. However, it will be appreciated that various changes in the details, materials and arrangements of parts, which have been herein described and illustrated in order to explain the nature of the subject matter, may be made by those skilled in the art without departing from the principle and scope of the subject matter, as expressed in the appended claims.

What is claimed is:

1. A composite tape from which a closure tab for disposable articles can be cut, the tape comprising:
    a fastening tape defining a distal end and an opposite proximal end, the fastening tape including a backing film, and an adhesive layer disposed on at least a portion of the backing film;
    a release tape defining a distal end and an opposite proximal end, the release tape including a backing film, an adhesive layer disposed on a first face of the backing film, a hinge component disposed at the proximal end of the release tape, the release tape also defining a second face oppositely directed from the first face;
    wherein the fastening tape and the release tape are sized and configured for attachment to one another such that the hinge component of the release layer contacts the adhesive layer of the fastening tape and is adhesively attached thereto, and the adhesive layer of the release tape is arranged in a pattern configuration
    wherein the pattern configuration includes a plurality of rows of adhesive, each adhesive row separated from immediately adjacent adhesive rows by a spacing row.

2. The composite tape of claim 1 wherein the length of the release tape is less than the length of the fastening tape.

3. The composite tape of claim 1 further comprising:
   an outwardly projecting finger lift disposed at a distal end of the fastening tape.

4. The composite tape of claim 3 wherein the finger lift is colored.

5. The composite tape of claim 1 wherein the distal end of the fastening tape has a serrated configuration.

6. The composite tape of claim 1 wherein the release tape is positioned relative to the fastening tape such that the distal end of the fastening tape extends beyond the distal end of the release tape.

7. The composite tape of claim 1 wherein the ratio of widths of the adhesive row to the spacing row is from about 0.5 to about 2.5:1.

8. The composite tape of claim 7 wherein the ratio is about 1.5:1.

9. The composite tape of claim 1 wherein the adhesive layer of the fastening tape is a continuous layer.

10. The composite tape of claim 1 wherein the composite tape is in roll form.

11. The composite tape of claim 1 wherein the fastening tape defines an adhesive-free region along a face of the backing film of the fastening tape directed toward the release tape and extending from the hinge component toward the proximal end.

12. The composite tape of claim 1 wherein the release tape defines an adhesive-free region along a face of the backing film of the release tape directed toward the fastening tape and extending from the hinge component toward the proximal end.

* * * * *